(12) United States Patent
Loske

(10) Patent No.: US 12,324,564 B2
(45) Date of Patent: Jun. 10, 2025

(54) PROTECTIVE SLEEVE

(71) Applicant: Lohmann & Rauscher GmbH, Vienna (AT)

(72) Inventor: Gunnar Loske, Ahrensburg (DE)

(73) Assignee: Lohmann & Rauscher GmbH, Vienna (AT)

( * ) Notice: Subject to any disclaimer, the term of this patent is extended or adjusted under 35 U.S.C. 154(b) by 738 days.

(21) Appl. No.: 17/266,297

(22) PCT Filed: Jul. 5, 2019

(86) PCT No.: PCT/EP2019/068131
§ 371 (c)(1),
(2) Date: Feb. 5, 2021

(87) PCT Pub. No.: WO2020/030353
PCT Pub. Date: Feb. 13, 2020

(65) Prior Publication Data
US 2021/0298578 A1 Sep. 30, 2021

(30) Foreign Application Priority Data
Aug. 10, 2018 (DE) .................... 20 2018 104 602.0

(51) Int. Cl.
*A61B 1/00* (2006.01)
*A61B 17/34* (2006.01)
(52) U.S. Cl.
CPC ...... *A61B 1/00135* (2013.01); *A61B 1/00066* (2013.01); *A61B 1/00154* (2013.01); *A61B 17/3421* (2013.01); *A61B 17/3423* (2013.01)

(58) Field of Classification Search
CPC ............ A61B 1/00135; A61B 1/00142; A61B 1/00154; A61B 1/00066; A61B 17/3421;
(Continued)

(56) References Cited

U.S. PATENT DOCUMENTS

| 1,662,227 A | 3/1928 | Noah |  |
|---|---|---|---|
| 4,694,826 A | * 9/1987 | Chester | ............ A61M 16/0488 600/185 |

(Continued)

FOREIGN PATENT DOCUMENTS

| DE | 10024660 A1 | 11/2000 |
| DE | 102014008128 A1 | 12/2014 |

(Continued)

OTHER PUBLICATIONS

International Search Report and Written Opinion mailed Feb. 13, 2020, for International Application No. PCT/EP2019/068131, 10 pages.

(Continued)

*Primary Examiner* — Ryan N Henderson
(74) *Attorney, Agent, or Firm* — Schwabe, Williamson & Wyatt, P.C.

(57) ABSTRACT

A protective sleeve (1) for an endoscopy device having a tubular hollow body (20) extending along a longitudinal axis (L) having a distal opening (23) on a distal end (22) insertable into a human or animal body and having a proximal opening (25) at the proximal end (24) opposite to the distal end (22), characterized in that the hollow body (20) has a holding arrangement (10) in the region of the proximal opening (25) for holding the protective sleeve (1).

13 Claims, 4 Drawing Sheets

(58) Field of Classification Search
CPC .......... A61B 17/3423; A61B 2017/345; A61B 17/3474; A61B 2017/3425; A61B 2017/3427; A61B 2017/3429; A61B 2017/3433; A61B 2017/3435; A61B 2017/3437; A61B 2017/3441; A61B 2017/3443; A61B 2017/3445; A61B 2017/3447; A61B 2017/3449; A61B 2017/3452; A61B 17/3431; A61B 17/3439

See application file for complete search history.

(56) References Cited

U.S. PATENT DOCUMENTS

| | | | | |
|---|---|---|---|---|
| 4,820,275 | A * | 4/1989 | Haber | A61M 5/326 604/232 |
| 5,249,568 | A | 10/1993 | Brefka et al. | |
| 5,364,408 | A * | 11/1994 | Gordon | A61B 17/06066 606/139 |
| 5,395,383 | A * | 3/1995 | Adams | A61F 2/0063 606/198 |
| 5,607,405 | A | 3/1997 | Decker et al. | |
| 5,730,756 | A * | 3/1998 | Kieturakis | A61F 2/0063 606/190 |
| 5,752,937 | A * | 5/1998 | Otten | A61M 25/0668 604/161 |
| 5,941,815 | A | 8/1999 | Chang | |
| 6,315,713 | B1 | 11/2001 | Takada | |
| 6,503,192 | B1 | 1/2003 | Ouchi | |
| 6,514,215 | B1 * | 2/2003 | Ouchi | A61B 10/04 600/564 |
| 8,709,021 | B2 * | 4/2014 | Chu | A61B 17/0469 606/144 |
| 8,932,260 | B2 * | 1/2015 | King | A61M 25/0668 604/167.03 |
| 9,687,142 | B1 | 6/2017 | Lieberman et al. | |
| 9,931,111 | B2 * | 4/2018 | Chu | A61B 17/0469 |
| 10,376,281 | B2 * | 8/2019 | Davis | A61B 1/06 |
| 11,051,924 | B2 * | 7/2021 | Miller | A61F 2/0045 |
| 11,738,179 | B2 * | 8/2023 | Bierman | A61M 25/0606 604/164.03 |
| 2003/0229269 | A1 | 12/2003 | Humphrey | |
| 2005/0256452 | A1 | 11/2005 | Demarchi et al. | |
| 2006/0041263 | A1 * | 2/2006 | Chu | A61B 17/0491 606/144 |
| 2007/0106118 | A1 | 5/2007 | Moriyama | |
| 2007/0250112 | A1 * | 10/2007 | Ravikumar | A61B 90/57 606/205 |
| 2009/0062614 | A1 * | 3/2009 | Adzich | A61B 1/31 600/129 |
| 2009/0069632 | A1 * | 3/2009 | McIntyre | A61B 1/0055 600/146 |
| 2010/0063359 | A1 | 3/2010 | Okoniewski | |
| 2010/0081877 | A1 * | 4/2010 | Vakharia | A61B 1/3132 600/129 |
| 2010/0312261 | A1 * | 12/2010 | Suzuki | A61J 15/0023 606/153 |
| 2011/0152625 | A1 * | 6/2011 | Smith | A61B 17/3462 600/208 |
| 2012/0053415 | A1 * | 3/2012 | Bunch | A61M 25/0136 600/121 |
| 2012/0071748 | A1 * | 3/2012 | Mark | A61B 17/3417 600/249 |
| 2014/0046134 | A1 * | 2/2014 | Kikuchi | A61B 1/00135 600/114 |
| 2014/0194685 | A1 * | 7/2014 | Riek | A61B 17/3498 600/114 |
| 2014/0236190 | A1 * | 8/2014 | Chu | A61B 17/0469 606/144 |
| 2015/0087914 | A1 | 3/2015 | Navis | |
| 2015/0151087 | A1 * | 6/2015 | Suzuki | A61J 15/0038 604/165.02 |
| 2015/0367103 | A1 * | 12/2015 | Pajunk | A61N 1/0551 604/512 |
| 2016/0022146 | A1 * | 1/2016 | Piron | A61B 5/0059 600/411 |
| 2017/0112371 | A1 | 4/2017 | Mcgown | |
| 2017/0265892 | A1 * | 9/2017 | Winegar | A61B 1/32 |
| 2018/0206866 | A1 * | 7/2018 | Wan | A61B 1/00 |
| 2019/0167299 | A1 * | 6/2019 | Davis | A61B 17/3421 |
| 2021/0030262 | A1 * | 2/2021 | Ito | A61B 1/00082 |
| 2021/0401457 | A1 * | 12/2021 | Schaefer | A61B 17/3462 |
| 2023/0200846 | A1 * | 6/2023 | Yazdi | A61M 5/158 604/164.03 |

FOREIGN PATENT DOCUMENTS

| | | | | |
|---|---|---|---|---|
| JP | 2009148554 A | * | 7/2009 | ......... A61B 17/3415 |
| WO | 2008/127886 A1 | | 10/2008 | |
| WO | 2011/038949 A1 | | 4/2011 | |
| WO | 2012/123414 A1 | | 9/2012 | |

OTHER PUBLICATIONS

International Preliminary Report on Patentability mailed Oct. 29, 2020, for International Application No. PCT/EP2019/068131, 10 pages.

Search Report issued Mar. 25, 2019 for DE Application No. 202018104602.0, 5 pages; machine translation generated by Google Translate on Feb. 5, 2025.

Issue Notification issued Jun. 21, 2019 for AT Application No. 501392018, 3 pages; machine translation generated by Google Translate on Feb. 5, 2025.

* cited by examiner

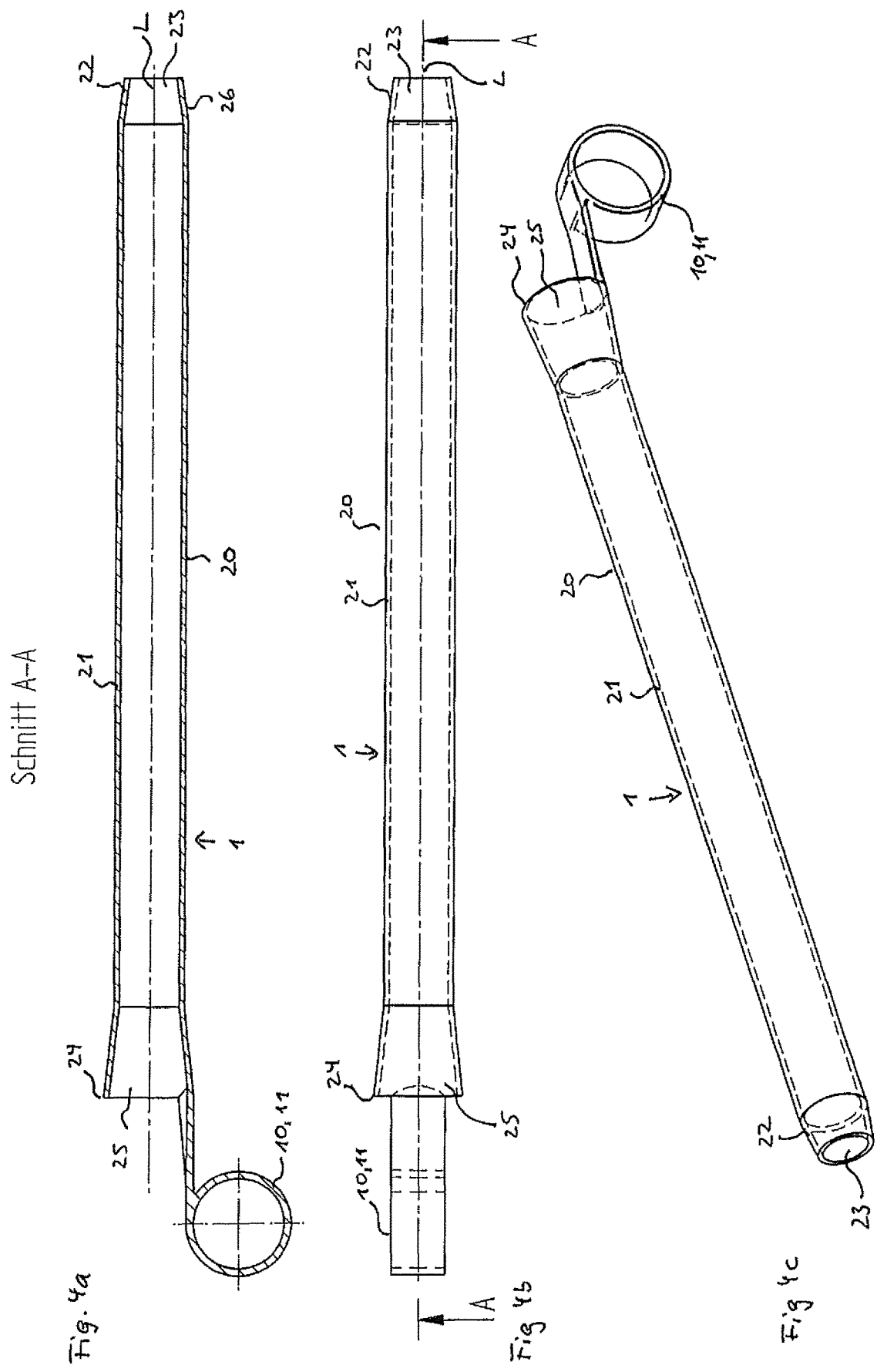

PROTECTIVE SLEEVE

CROSS REFERENCE TO RELATED APPLICATION

The present application is a 35 U.S.C. § 371 national phase entry application of, and claims priority to, International Patent Application No. PCT/EP2019/068131, filed Jul. 5, 2019, which claims priority to German Patent Application No. DE 202018104602.0, filed Aug. 10, 2018, the disclosures of which are hereby incorporated by reference in their entirety for all purposes.

BACKGROUND

The invention relates to a protective sleeve for an endoscopic device with a tubular body extending along a longitudinal axis, which has a distal opening at a distal end which can be inserted into a human or animal body and a proximal opening at a proximal end opposite the distal end.

Such protective sleeves, also known as overtubes, are known from the prior art, for example from WO 2011/038949 and WO 2012/123414, and are used in endoscopic examinations, in particular together with flexible endoscopes. Additionally or alternatively, generic protective sleeves can also be used together with rigid endoscopes. Preferably, generic protective sleeves are used in conjunction with flexible gastroscopes, colonoscopes and enteroscopes. An important area of application of such protective sleeves is examination on the upper gastrointestinal tract (esophagus, stomach, duodenum and small intestine). The protective sleeve is inserted with its distal end from a natural or artificial body opening into the body and forms an access into the body. Along this access, items such as endoscopes, instruments, drains, etc. may be inserted into or removed from the body. The protective sleeve protects the body tissue, such as the intestinal wall, from injury when entering and removing objects into or out of the body.

For example, a protective sleeve may be pushed through the mouth over the throat along the esophagus to the stomach or even to the bowel. The endoscope can serve as a splint for the protective sleeve. In a typical examination maneuver, the protective sleeve is first pushed over the endoscope, then the endoscope is inserted into the body and then the protective sleeve is pushed along the endoscope into the body. The protective sleeve can also be introduced together with the endoscope under endoscopic view into the intestine. Alternatively, the protective sleeve can be placed by means of a mandrel, a guide wire or an insertion tool. The placement can also be done by means of monitoring with an X-ray machine.

A protective sleeve offers various applications. Thus, with the protective sleeve, the upper intestinal organs from the mouth to the small intestine as well as anatomically caused tightness, such as the esophageal inlet, the upper and distal esophageal sphincter and the pylorus can be bridged. However, uses of the protective sleeve in the lower gastrointestinal tract are also known. The protective sleeve is also used in the so-called endoscopic negative pressure therapy to lead especially for vacuum treatment suitable drainages, such as open-pore foam drains or open-pore film drains to an intracorporal wound site. In the lower gastrointestinal tract, for example, an anastomotic leak after rectal resection can be treated with endoscopic negative pressure therapy. The anus and the rectum are bridged with the protective sleeve. The vacuum drainages or other instruments to be inserted, drains, bodies, etc. can be brought to the intracorporal wound site along the lumen of the protective sleeve with the aid of a pusher or the endoscope. This procedure is also used in the upper gastrointestinal tract. At the upper gastrointestinal tract, for example, anastomotic leakages following esophageal resection or esophageal perforations may be treated with negative pressure therapy. Along the inserted protective sleeve, suitable drainage tubes are introduced for the negative pressure therapy. Using generic protective sleeves, drains or other instruments to be inserted etc. can also be introduced with the aid of endoscopic gripping instruments or even without additional instruments. They can be introduced with the help of an endoscope.

Depending on the field of application, the protective sleeves can have different diameters and have lengths in the range of 3 to 150 cm, in particular 10 to 150 cm. If protective sleeves with a short length (e.g. 15 to 35 cm) are used during an endoscopic examination, there is a risk that the protective sleeve will be inserted into the body with the endoscope so that it lies completely inside the body. This danger exists in particular in endoscopic negative pressure therapy of the upper gastrointestinal tract. In this method, protective sleeves with a short length are used, which serve the bridging of the throat and mouth to the esophagus, and vacuum drains, in particular open-pore foam drains, are attached with a pusher or at the distal end of an endoscope, in particular flexible endoscope, such as gastroscopes, and advanced along the protective sleeve through the mouth and along the pharyngeal curvature into the esophagus or stomach. The attachment to the distal end of an endoscope, e. g. gastroscope, can be effected by gripping with an endoscopic gripping instrument (polyp gripper, forceps, snare or the like). The attachment may be releasably designed so that the drains can be released after placement at the placement location. Especially drains with voluminous and long foam elements experience a certain frictional resistance during insertion and advancement, and there is a risk that such drainages jam in the protective sleeve. When inserting and advancing the vacuum drainage in (to) the protective sleeve, therefore, the proximal end of the protective sleeve, which projects out of the body opening (e. g. mouth, anus, wound), is fixed, for example with a hand or a gripping instrument. The fixing is intended to prevent the protective sleeve from being completely inserted into the body beyond the insertion opening of the body surface. When trying to move the vacuum drainage against the frictional resistance of the protective sleeve, the protective sleeve, which is held at its proximal end by hand, may accidentally slip too deep into the body and thus dislocate into the body depth.

Moreover, when inserting the protective sleeve itself over the body opening (anus, mouth, wound), it may happen that the sleeve completely slides into the body and thus is inserted too deep beyond the body surface. The protective sleeve can then dislocate intracorporally.

Removing a protective sleeve inserted too deep from the body can be difficult. Attempting to remove the protective sleeve may lead to mucosal injuries or even to transmural intestinal injuries (iatrogenic perforations). The removal of the protective sleeve is made more difficult in particular by the fact that both the protective sleeve and the endoscope are generally provided with a lubricant for the purpose of facilitating insertion. If endoscopic removal does not succeed in dislocation, in the worst case surgical removal may be necessary. Uncontrolled intracorporal dislocation can also lead to severe injuries in the sense of transmural perforations. These injuries are known from treatment with gastrointestinal stents. A particularly serious complication of a too deeply inserted protective sleeve may be the blocking of the respiratory tract through the protective sleeve. This is a life-threatening complication.

In order to solve the problems described above, in the past tools such as pliers and/or clamps have been used to fix the protective sleeve at the proximal end and prevent it from slipping. However, these tools can damage the protective sleeve, which also poses a risk of injury to the patient.

Also the equipment with a removal or security thread or strap is conceivable. However, this causes a considerable risk of injury. This is created by cutting the removal or security thread or strap into the tissue. Moreover, when the protective sleeve is withdrawn from the body, there is a considerable traumatic risk of injury due to the dislocated proximal end of the protective sleeve.

Using forceps or clamps may damage the integrity of the sleeve itself. This can lead to the breakage of wall elements, the formation of sharp edges, the exposure of wire elements of the sleeve wall and the like.

Protective sleeves for protecting an endoscopic or laparoscopic instrument are disclosed in DE 102014008128 A1 and US 2010/0063359 A1.

Protective sleeves as specified in the pre-characterizing portion of amended claim 1 are disclosed in US 2005/0256452 A1.

In view of these problems in the prior art, it is the object of the present invention to provide protective sleeves for use with an endoscopy device, which reduce the risk of injury to the patient.

This problem is inventively achieved by a development of the protective sleeve as specified in the characterizing portion of appended claim 1.

The invention is based on the finding that the protective sleeve can be securely held and controlled through the holding arrangement by one person. By means of the holding arrangement, the protective sleeve introduced with its distal end into a human or animal body can be selectively pushed back and forth in the distal direction and thus fixed in the body at a predetermined penetration depth. The protective sleeve can preferably be provided with a height marking, from which the penetration depth of the protective sleeve can be read off. By the holding arrangement, the user can reliably hold the protective sleeve in the desired position during the insertion of an object, for example an endoscope. The holding arrangement also facilitates removal of the protective sleeve from the body by transmitting a tensile force acting in the longitudinal direction via the holding arrangement to the hollow body.

The protective sleeve can also be rotated around its longitudinal axis by the holding arrangement. As a result, bodily constrictions can be overcome more easily.

The holding arrangement can protrude from the hollow body in the radial direction to the outside. This prevents the protective sleeve to be inserted too deep and to rest completely inside the body.

In any case, the holding arrangement is designed such that the function of the protective sleeve, and in particular the insertion of objects through the protective sleeve, is not hindered by the holding arrangement. In particular, the holding arrangement is arranged such that the inner diameter of the protective sleeve is not reduced.

In an embodiment of the invention, the holding arrangement can be extending in a circumferential direction transversely to the longitudinal axis by less than 360°, preferred by less than 270°, particularly preferred by less than 180°, even more particularly preferred by less than 90°, particularly preferred by less than 45° along a wall of the hollow body. The holding arrangement thus does not extend completely around the hollow body in the circumferential direction. This embodiment allows a particularly secure gripping of the holding arrangement with one hand and thus a particularly reliable fixation and control of the protective sleeve.

The wall of the hollow body may at least in regions have a profiling on an outer side and/or on an inner side. In this case, a profile extending in the longitudinal direction or a notch extending along the longitudinal direction may be provided on the outside of the wall. As a result, insertion of the protective sleeve into the body can be simplified, since the frictional resistance can be reduced by such a profile. In order to increase the frictional resistance and thereby prevent slippage of the protective sleeve inserted into the body, a transversely extending profile or a transversely extending longitudinal notch may be provided on the outside of the wall. Alternatively, a helical profile may be provided on the outside of the wall. This promotes insertion of the protective sleeve into the body with a helical movement while increasing the frictional resistance in the longitudinal direction, whereby slipping of the inserted protective sleeve can be prevented. In addition, such a profile favors the removal of the protective sleeve from the body with a helical movement.

Additionally or alternatively, a profile may be provided in the wall on the inside of the hollow body. To facilitate insertion of objects through the protective sleeve, a longitudinally extending profile or a longitudinally extending notch may be provided on the inside of the wall. Such a profile reduces the friction between the object to be inserted and the inside of the wall. To facilitate insertion of an object in a helical motion, a helical profile may be formed on the inside of the wall.

The holding arrangement can be releasably connected to the hollow body. The connection may be formed, for example, as a bayonet connection, as a screw connection or as a plug connection. The holding arrangement can also be adhesively connected to the hollow body. The compound is designed such that a tensile, shear and torsional strength is present. The holding arrangement can also be permanently and inextricably connected to the hollow body. For example, the holding arrangement may be formed in one piece with the hollow body. Advantageously, the connection between the holding arrangement and the hollow body is seamless, i. e. formed without a sharp-edged passage. As a result, even if the protective sleeve is inserted very deeply into the body and the holding arrangement comes into contact with the body tissue, superficial tissue injuries are avoided. The holding arrangement may be arranged on the outside of the hollow body on the wall thereof. Alternatively, however, the holding arrangement can also be arranged on the inside of the hollow body on its wall, or it can be placed on an edge of the proximal opening on the protective sleeve. The holding arrangement can—possibly subsequently—be mounted so that the function of the overtube or the introduction of components is not hindered. Advantageously, the inner lumen of the overtube is not reduced by the holding arrangement.

Preferably, the holding arrangement is configured in a form that allows easy gripping. In one embodiment of the invention, the holding arrangement may take the form of a tab extending away from the hollow body. The tab can then be attached, for example be glued, to the outside of the wall.

Particularly advantageously, the holding arrangement is configured in a form which allows holding the protective sleeve with only one hand, and particularly preferably with only one finger. For this purpose, the holding arrangement may have a grip loop. The grip loop can be completely formed circumferentially around the hollow body. However, it can also extend only along a section in the circumferential direction, preferably by less than 45° along the wall of the hollow body extending in a circumferential direction transverse to the longitudinal axis. In one embodiment, the handle loop is formed as a closed loop. This means that the grip loop completely extends along a transverse axis, in particular approximately perpendicular to the longitudinal axis. This allows gripping with just one finger. The closed handle loop may be designed annular in one embodiment. The ring may be formed circumferentially parallel or transverse to the longitudinal axis of the protective sleeve. An inner diameter of the ring may be 1.5 to 5.0 cm, especially 2.0 to 3.0 cm.

The handle loop can also be designed to be open. This means that the grip loop only partially extends along the transverse axis, in particular approximately perpendicular to the longitudinal axis. The open handle loop allows grasping with multiple fingers. The handle loop may extend along the entire circumference of the protective sleeve. As a result, particularly large tensile forces can be exerted on the protective sleeve without damaging the protective sleeve. However, the grip loop can extend only along a region of the protective sleeve by less than 360°, preferably by less than 90°, particularly preferably by less than 45° along the wall. This allows operation with only a few fingers.

However, the holding arrangement may also have a rod-shaped, pistol grip-like configuration or a rod-shaped, handgrip-shaped configuration.

Furthermore, a surface of the holding arrangement can be profiled at least in regions. As a result, the grip of the holding arrangement can be improved, since an increase in the frictional resistance can be achieved by the profiling.

According to this invention, the wall of the hollow body is reinforced with a helix. The helix comprises a metal wire. This reduces bowing of the protective sleeve during insertion of an object.

In one embodiment of the invention, the hollow body and the holding arrangement of the protective sleeve may have the same material, in particular consist of the same material.

The holding arrangement may be formed of a transparent material. Such a designed holding arrangement affects the view of a user only slightly. A writing may be provided on the holding arrangement.

In one embodiment of the invention, an extension of the holding arrangement in the direction of the longitudinal axis is at least 2 cm, preferably at least 3 cm, and at most 10 cm, in particular at most 7 cm, preferably at most 6 cm. The holding arrangement can extend the hollow body in the axial direction accordingly. In such an embodiment of the holding arrangement, it can be held with one finger, while the rest of the hand leads the endoscope.

Further, it is advantageous if the distal end of the hollow body is tapered. In addition, it is advantageous if the edge of the distal opening is rounded. By these embodiments, a tissue-conserving advancing of the protective sleeve in the body is ensured.

Further, it is advantageous if the proximal end of the protective sleeve widens in a funnel shape. This facilitates insertion of objects such as an endoscope.

The protective sleeve may have a length between 10 cm and 150 cm, in particular between 20 cm and 120 cm. A protective sleeve of this length can be introduced in the upper gastrointestinal tract, in the mouth and throat but also in the upper esophageal area to the duodenum.

In a further embodiment of the invention, the wall of the protective sleeve may have a slot extending in the longitudinal direction. The slot can be closed. For example, the slot may be opened and closed by a zipper-type mechanism. The slot makes it possible to insert an object, for example an endoscope, laterally into and out of the hollow body, which increases the flexibility of the use of the protective sleeve.

In the wall of the protective sleeve, additional channels extending preferably parallel to the protective sleeve axis may be provided. These channels can be used to rinse, suck or insert endoscopic instruments, guidewires and the like.

BRIEF DESCRIPTION OF THE DRAWINGS

In the following, the invention will be explained with reference to the drawing, to which reference is expressly made with respect to all details essential to the invention and details of which are not further elaborated in the description. In the drawing shows.

DETAILED DESCRIPTION

Figure 1:
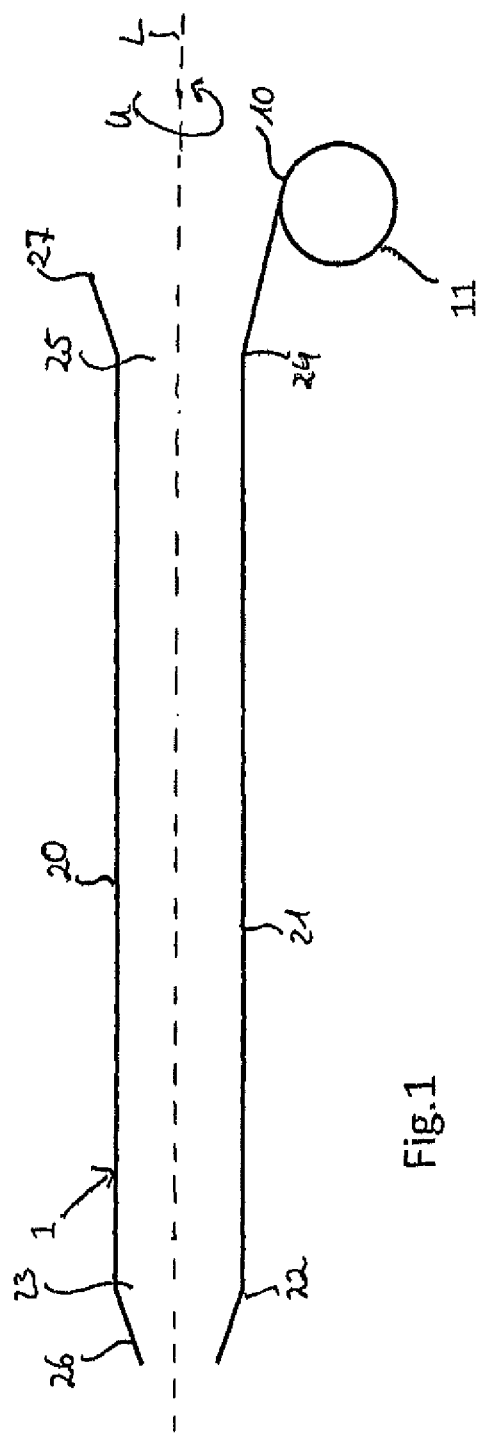
FIG. 1 a schematic side view of a first embodiment of a protective sleeve according to the invention, FIG. 2 a schematic side view of a second embodiment of a protective sleeve according to the invention FIG. 3 a schematic side view of a third embodiment of a protective sleeve according to the invention, FIG. 4a a sectional view of a fourth embodiment of a protective sleeve according to the invention, FIG. 4b a side view of the fourth embodiment of the protective sleeve shown in FIG. 4a, and FIG. 4c a perspective view of the fourth embodiment of the protective sleeve shown in FIGS. 4a and 4b.

FIG. 1 shows a schematic side view of a first embodiment of a protective sleeve 1 according to the invention. The protective sleeve 1 has a tubular hollow body 20 with a wall 21 which extends between a distal end 22 and a proximal end 24 in a longitudinal direction L. The hollow body 20 has a distal opening 23 at the distal end 22 and a proximal opening 24 at the proximal end 24. The protective sleeve 1 may be formed in one embodiment of a soft plastic, such as silicone or PVC, which has a Shore A hardness of 30 to 70, preferably 40 to 60.

The protective sleeve 1 can be inserted with its distal end 22 into a human or animal body. In order to simplify the insertion of the protective sleeve 1, the protective sleeve 1 has at its distal end 22 a tapered tip 26. At its proximal end 24, the protective sleeve 1 has a funnel-shaped region 27. The funnel-shaped enlargement at the proximal end 24 of the tubular hollow body 20 facilitates insertion of an object into the protective sleeve 1. However, the protective sleeve 1 can also be formed without the tapered tip 26 and without the funnel-shaped region 27.

Further, at the proximal end 24 of the protective sleeve 1, a holding arrangement 10 is arranged. The holding arrangement 10 has a closed handle loop 11, which extends in a circumferential direction transverse to the longitudinal axis L by less than 90° along the wall 21. The closed handle loop 11 can be gripped with just one finger, whereby a particularly simple fixation and movement of the protective sleeve 1, even when using a lubricant gel, is made possible. Due to the closed loop shape, the holding assembly 11 may have sufficient stability even with a small material thickness and when using a soft material. Thus, the same soft material can be used for the handle loop 11 as for the hollow body 20.

Then, the handle loop 11 can be integrally formed with the hollow body 20. This facilitates the production and saves costs.

Figure 2:
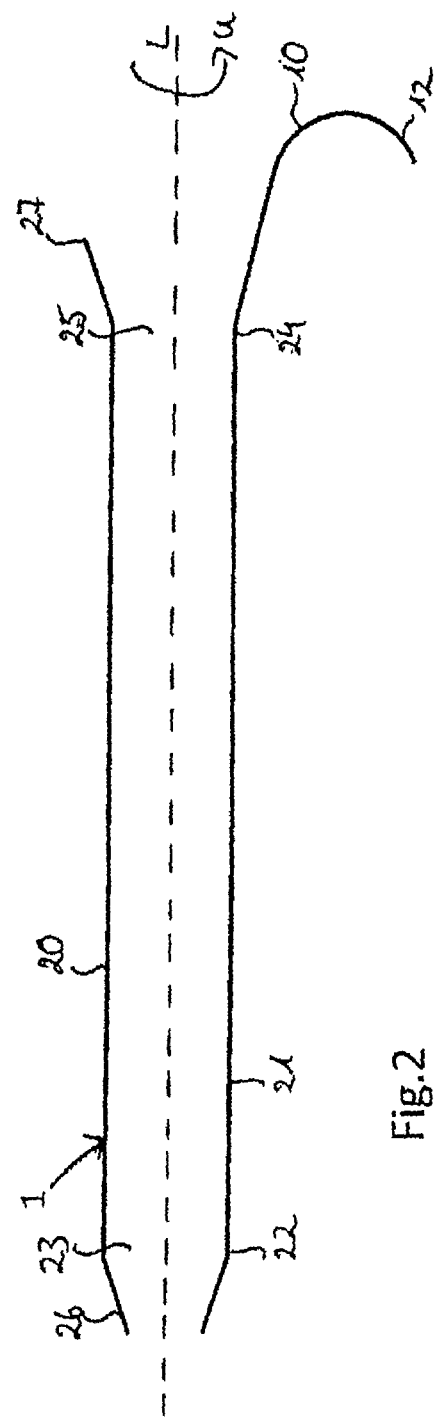

The second embodiment of a protective sleeve illustrated in FIG. 2 according to the invention differs from the embodiment shown in FIG. 1 only by the configuration of the holding arrangement 10, so that the description of the remaining components of the protective sleeve 1 is not repeated. The holding arrangement 10 of the second embodiment has an open handle loop 12. If the grip loop 12 is formed from the same soft material as the hollow body 20, the grip loop 12 must be gripped with several fingers to safely guide or fix the protective sleeve 1. In order to allow handling of the protective sleeve 1 with only one finger, as in the first embodiment, the handle loop 12 must be formed of a harder material. Again, the handle loop 12 does not extend around the entire circumference of the hollow body 20, but the grip loop 12 extends only by less than 90° along the wall 21.

Figure 3:
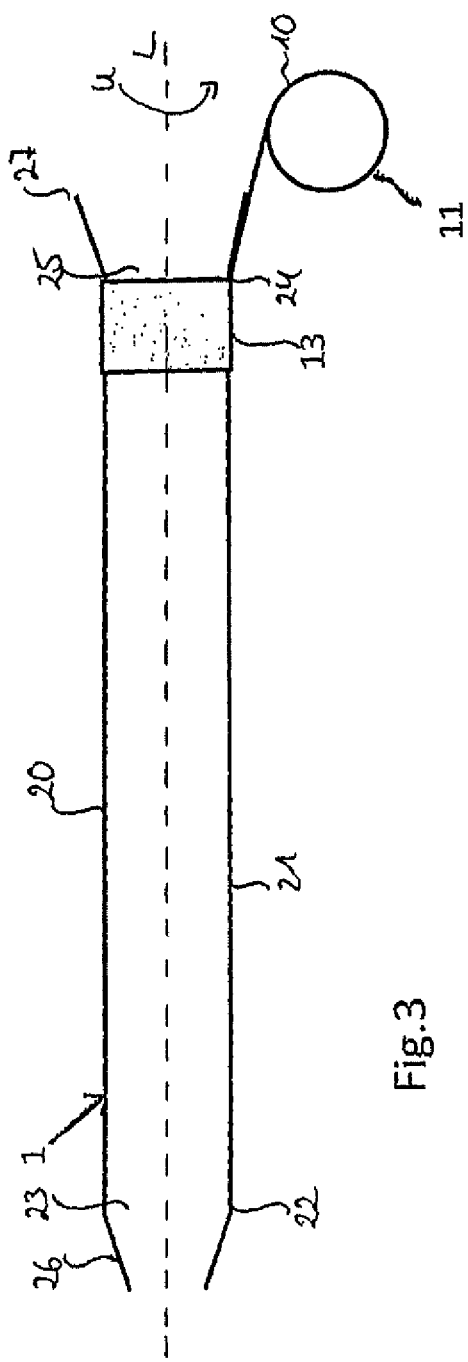

In the schematic side view shown in FIG. 3 of a third embodiment of a protective sleeve 1 according to the invention, the holding arrangement 10, as in the first embodiment shown in FIG. 1, has a closed grip loop 11. In contrast to the first embodiment, however, in the third embodiment, the holding arrangement 10 extends around the entire circumference of the hollow body 20 and is secured to the outside of the hollow body 20 with a circumferential mounting ring 13, to which the handle loop 11 is attached. By attaching the handle loop 11 by means of the circumferential fastening ring 13, higher tensile forces due to a more uniform force distribution can be achieved without damaging the protective sleeve 1. The mounting ring 13 may allow a releasable attachment of the holding arrangement 10 to the protective sleeve 1. The attachment can also be designed inextricable.

Also in the case of the fourth embodiment of a protective sleeve 1 according to the invention shown in FIGS. 4 *a*-4 *c*, the holding arrangement 10 has a closed grip loop 11. The grip loop is attached to the outside of the protective sleeve 1 as in the third embodiment of the invention. However, as in the first embodiment, the holding arrangement 10 does not extend along the entire circumference but only by less than 45° along the wall 21.

The invention claimed is:

1. A protective sleeve for use with an endoscopy device, wherein the protective sleeve comprises:
    a tubular hollow body that extends along a longitudinal axis, wherein the tubular hollow body includes:
        a distal opening on a distal end that is insertable into a human or animal body; and
        a proximal opening at a proximal end that is opposite to the distal end, the proximal end configured to removably receive the endoscopy device therein; and
    a holding arrangement coupled with the hollow body, wherein the holding arrangement is in a region of the proximal opening for holding the protective sleeve;
    wherein the wall of the hollow body is reinforced with a wire helix that includes a metal wire;
    wherein the hollow body and the holding arrangement have a same material, and the holding arrangement is made of a transparent material or a semi-transparent material; and
    wherein the holding arrangement includes a grippable element in which at least a portion of a finger of a user may be at least partially inserted during use.

2. The protective sleeve of claim 1, wherein the holding arrangement in a circumferential direction transverse to the longitudinal axis extends by less than 45° along a wall of the hollow body.

3. The protective sleeve of claim 1, wherein a wall on an outer side of the hollow body is at least partially profiled.

4. The protective sleeve of claim 1, wherein the holding arrangement is detachably coupled with the hollow body.

5. The protective sleeve of claim 1, wherein the grippable element includes a closed grip loop.

6. The protective sleeve of claim 1, wherein a surface of the holding arrangement is profiled at least in regions.

7. The protective sleeve of claim 1, wherein the holding arrangement is made of a material having a Shore A hardness of more than 70.

8. The protective sleeve of claim 1, wherein the extension of the holding arrangement in the direction of the longitudinal axis is between 2 centimeters (cm) and 10 cm.

9. The protective sleeve of claim 1, wherein a wall on an inner side of the hollow body is at least partially profiled.

10. The protective sleeve of claim 1, wherein the grippable element includes a loop.

11. The protective element of claim 1, wherein the grippable element has an axis that is not coincident with a longitudinal axis of the tubular hollow body.

12. The protective element of claim 11, wherein the axis of the grippable element is not parallel to the longitudinal axis of the tubular hollow body.

13. The protective element of claim 11, wherein the axis of the grippable element is transverse to the longitudinal axis.

* * * * *